United States Patent
Gruss (10) Patent No.: US 8,134,032 B2
(45) Date of Patent: Mar. 13, 2012

(54) CRYSTALLINE MODIFICATIONS OF (1R,2R)-3-(3-DIMETHYLAMINO-1-ETHYL-2-METHYL-PROPYL)-PHENOL

(75) Inventor: Michael Gruss, Aachen (DE)

(73) Assignee: Gruenenthal GmbH, Aachen (DE)

( * ) Notice: Subject to any disclaimer, the term of this patent is extended or adjusted under 35 U.S.C. 154(b) by 501 days.

(21) Appl. No.: 12/329,111

(22) Filed: Dec. 5, 2008

(65) Prior Publication Data

US 2009/0149534 A1    Jun. 11, 2009

Related U.S. Application Data

(60) Provisional application No. 61/012,295, filed on Dec. 7, 2007.

(30) Foreign Application Priority Data

Dec. 7, 2007  (EP) .................................... 07023728

(51) Int. Cl.
  *C07C 29/74*  (2006.01)

(52) U.S. Cl. ........ 568/810; 564/355; 568/700; 568/702; 568/715

(58) Field of Classification Search ........................ None
  See application file for complete search history.

(56) References Cited

U.S. PATENT DOCUMENTS 6,248,737 B1 * 6/2001 Buschmann et al. ...... 514/231.8
2007/0213405 A1 * 9/2007 Fischer et al. ................ 514/649

FOREIGN PATENT DOCUMENTS

| EP | A-0 693 475 | 1/1996 |
| EP | 1 612 203 A | 1/2006 |

OTHER PUBLICATIONS

European Search Report dated Apr. 29, 2008 (Six (6) pages).
International Search Report dated Mar. 13, 2009 (Three (3) pages).

* cited by examiner

*Primary Examiner* — Sudhakar Katakam
(74) *Attorney, Agent, or Firm* — Crowell & Moring LLP (57) ABSTRACT

Crystalline modifications of (1R,2R)-3-(3-dimethylamino-1-ethyl-2-methyl-propyl)-phenol, pharmaceutical compositions which contain these modifications, and the use thereof to treat pain or other conditions.

27 Claims, 5 Drawing Sheets

CRYSTALLINE MODIFICATIONS OF (1R,2R)-3-(3-DIMETHYLAMINO-1-ETHYL-2-METHYL-PROPYL)-PHENOL

BACKGROUND OF THE INVENTION

The invention relates to crystalline modifications of (1R,2R)-3-(3-dimethylamino-1-ethyl-2-methyl-propyl)-phenol, pharmaceutical compositions which contain these modifications, and the use thereof.

(1R,2R)-3-(3-dimethylamino-1-ethyl-2-methyl-propyl)-phenol is a synthetic analgesic which is used for the treatment of severe to very severe, acute and chronic pains. The compound can in this case be used in the form of the free base thereof or in the form of pharmaceutically acceptable salts and solvates. The production of the compound and the salts thereof is known from U.S. Pat. No. 6,248,737 (=EP 693,475), the compound normally being obtained in the form of a salt thereof, for example in the form of the hydrochloride thereof.

SUMMARY OF THE INVENTION

It is an object of the present invention to provide free base of (1R,2R)-3-(3-dimethylamino-1-ethyl-2-methyl-propyl)-phenol in a novel crystalline form.

Another object of the invention is to provide crystalline (1R,2R)-3-(3-dimethylamino-1-ethyl-2-methyl-propyl)-phenol in high yields and with high purity.

These and other objects have been achieved in accordance with the invention as described and claimed hereinafter.

It has surprisingly been found that under suitable conditions the compound (1R,2R)-3-(3-dimethylamino-1-ethyl-2-methyl-propyl)-phenol can be obtained in a crystalline form, in particular in the form of the polymorphs A, B and C disclosed hereinafter.

These crystalline forms make it possible to obtain the compound (1R,2R)-3-(3-dimethylamino-1-ethyl-2-methyl-propyl)-phenol in the form of the free base, with high yields and high purity. These forms are further distinguished in that they are very easy to handle and allow an exact metering of the active ingredient.

Moreover, different polymorphs of said pharmaceutical active ingredient have fundamentally different properties, which may provide further advantages.

On the one hand, the advantages may be based on a particular physical property of a particular modification, for example in relation to the handling or storage thereof, for example thermodynamic stability; crystal morphology, in particular structure, size, colour; density; bulk density; hardness; deformability; calorimetric characteristics, in particular melting point; solubility properties, in particular intrinsic rate of dissolution and equilibrium solubility; hygroscopicity; relative moisture profile; adhesion etc.

On the other hand, the crystalline modifications may also have improved chemical properties. For example, it is known that a lower hygroscopicity can lead to improved chemical stability and longer storage lives for chemical compounds.

One aspect of the present invention therefore relates to a crystalline modification of (1R,2R)-3-(3-dimethylamino-1-ethyl-2-methyl-propyl)-phenol.

A further aspect of the present invention relates to a crystalline modification A of (1R,2R)-3-(3-dimethylamino-1-ethyl-2-methyl-propyl)-phenol which has an X-ray diffraction peak at 15.58±0.20 (2Θ).

Preferably, the crystalline modification A according to the invention may additionally have at least one X-ray diffraction peak selected from the group consisting of 28.37±0.20 (2Θ) and 34.45±0.20 (2Θ).

The crystalline modification A according to the invention may further be characterized in that as well as the X-ray diffraction peak at 15.58±0.20 (2Θ) and optionally one or more X-ray diffraction peaks selected from the group consisting of 28.37±0.20 (2Θ) and 34.45±0.20 (2Θ), it additionally has at least one X-ray diffraction peak selected from the group consisting of 13.71±0.20 (2Θ), 14.80±0.20 (2Θ), 16.89±0.20 (2Θ), 17.79±0.20 (2Θ), 18.45±0.20 (2Θ), 20.20±0.20 (2Θ), 20.92±0.20 (2Θ), 22.50±0.20 (2Θ), 24.37±0.20 (2Θ) and 25.33±0.20 (2Θ).

Furthermore, the crystalline modification A according to the invention may be characterized in that as well as the X-ray diffraction peak at 15.58±0.20 (2Θ) and optionally one or more X-ray diffraction peaks selected from the group consisting of 28.37±0.20 (2Θ) and 34.45±0.20 (2Θ) and optionally one or more X-ray diffraction peaks selected from the group consisting of 13.71±0.20 (2Θ), 14.80±0.20 (2Θ), 16.89±0.20 (2Θ), 17.79±0.20 (2Θ), 18.45±0.20 (2Θ), 20.20±0.20 (2Θ), 20.92±0.20 (2Θ), 22.50±0.20 (2Θ), 24.37±0.20 (2Θ) and 25.33±0.20 (2Θ), it additionally has at least one X-ray diffraction peak selected from the group consisting of 14.11±0.20 (2Θ), 19.07±0.20 (2Θ), 21.12±0.20 (2Θ), 21.90±0.20 (2Θ), 22.21±0.20 (2Θ), 24.75±0.20 (2Θ), 27.32±0.20 (2Θ), 27.55±0.20 (2Θ), 29.90±0.20 (2Θ) and 30.68±0.20 (2Θ).

The crystalline modification A according to the invention may also be characterized in that as well as the X-ray diffraction peak at 15.58±0.20 (2Θ) and optionally one or more X-ray diffraction peaks selected from the group consisting of 28.37±0.20 (2Θ) and 34.45±0.20 (2Θ) and optionally one or more X-ray diffraction peaks selected from the group consisting of 13.71±0.20 (2Θ), 14.80±0.20 16.89±0.20 (2Θ), 17.79±0.20 (2Θ), 18.45±0.20 (2Θ), 20.20±0.20 (2Θ), 20.92±0.20 (2Θ), 22.50±0.20 (2Θ), 24.37±0.20 (2Θ) and 25.33±0.20 (2Θ), and optionally one or more X-ray diffraction peaks selected from the group consisting of 14.11±0.20 (2Θ), 19.07±0.20 (2Θ), 21.12±0.20 (2Θ), 21.90±0.20 (2Θ), 22.21±0.20 (2Θ), 24.75±0.20 (2Θ), 27.32±0.20 (2Θ), 27.55±0.20 (2Θ), 29.90±0.20 (2Θ) and 30.68±0.20 (2Θ), it additionally has at least one X-ray diffraction peak selected from the group consisting of 16.31±0.20 (2Θ), 23.30±0.20 (2Θ), 24.04±0.20 (2Θ), 28.05±0.20 (2Θ), 29.62±0.20 (2Θ), 30.28±0.20 (2Θ), 31.43±0.20 (2Θ), 32.21±0.20 (2Θ), 32.98±0.20 (2Θ), 33.41±0.20 (2Θ), 33.76±0.20 (2Θ), 34.17±0.20 (2Θ), 35.98±0.20 (2Θ), 36.24±0.20 (2Θ), 36.54±0.20 (2Θ), 36.87±0.20 (2Θ), 37.06±0.20 (2Θ), 37.48±0.20 (2Θ), 37.87±0.20 (2Θ), 38.64±0.20 (2Θ) and 39.48±0.20 (2Θ).

Preferably, the crystalline modification A according to the invention may be characterized in that it does not have one or more of the following X-ray diffraction peaks selected from the group consisting of 10.93±0.20 (2Θ), 12.41±0.20 (2Θ), and 26.22±0.20 (2Θ).

It is also preferable for the crystalline modification A according to the invention to be further characterized in that it does not have one or more of the following X-ray diffraction peaks selected from the group consisting of 8.10±0.20 (2Θ), 10.93±0.20 (2Θ), 11.83±0.20 (2Θ), 12.41±0.20 (2Θ), 26.22±0.20 (2Θ), 26.54±0.20 (2Θ) and 26.72±0.20 (2Θ).

Figure 1:
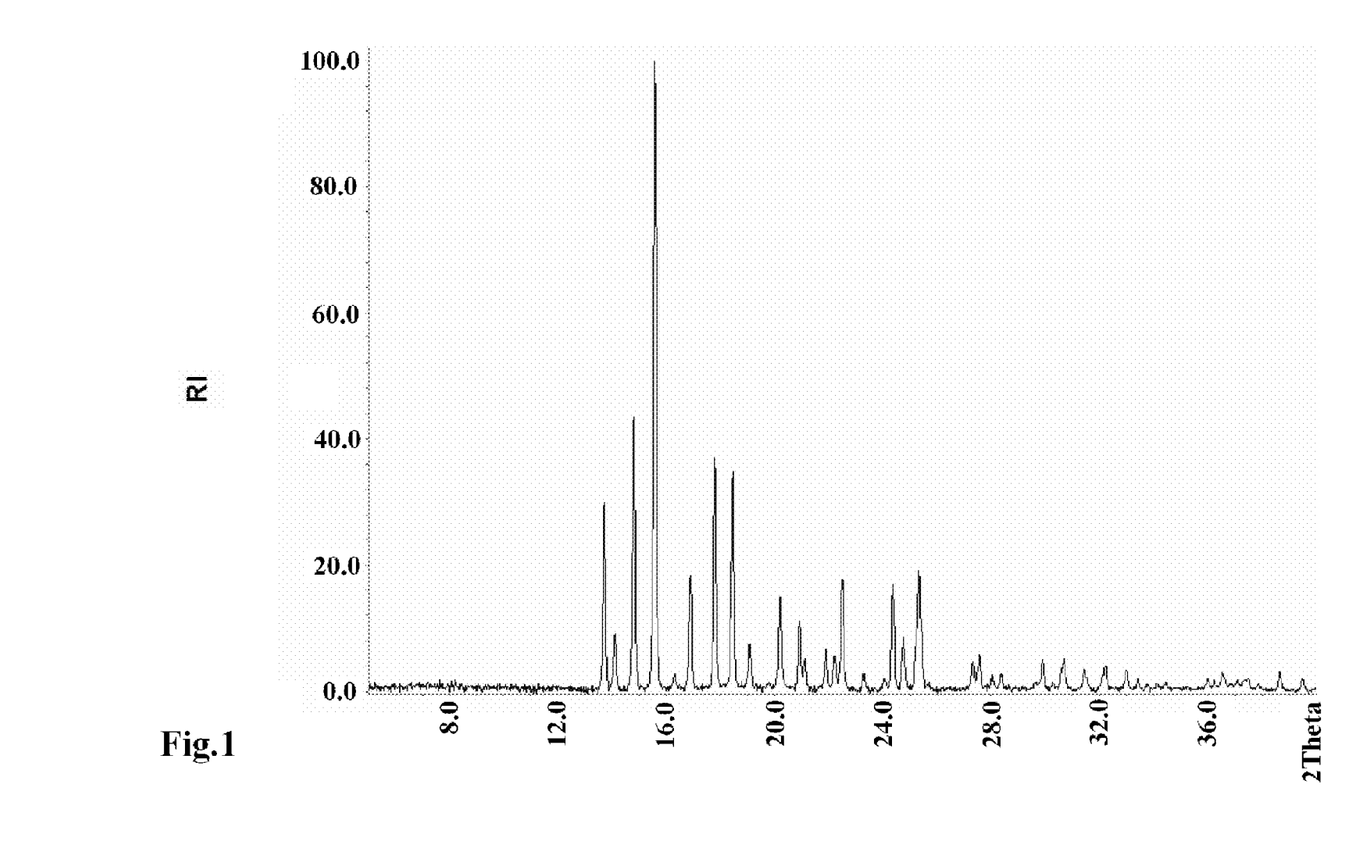
FIG. 1 shows an XRPD spectrum of crystalline modification A.

FIG. 1 shows an X-ray powder diffractogram of crystalline modification A.

In differential scanning calorimetry (DSC) analyses, the crystalline modification A according to the invention preferably exhibits endothermy with a peak temperature at 75-84° C., more preferably at 76-83° C., even more preferably at 77-82° C. and in particular at 78-81° C.

The crystalline form A according to the invention may further be characterized in that it has one or more Raman bands selected from the group consisting of $104\pm2$ cm$^{-1}$, $249\pm2$ cm$^{-1}$, $536\pm2$ cm$^{-1}$, $724\pm2$ cm$^{-1}$, $830\pm2$ cm$^{-1}$, $999\pm2$ cm$^{-1}$, $1283\pm2$ cm$^{-1}$, $1462\pm2$ cm$^{-1}$, $1584\pm2$ cm$^{-1}$, $2790\pm2$ cm$^{-1}$, $2839\pm2$ cm$^{-1}$, $2873\pm2$ cm$^{-1}$, $2933\pm2$ cm$^{-1}$, $2965\pm2$ cm$^{-1}$ and $3045\pm2$ cm$^{-1}$.

Figure 2:
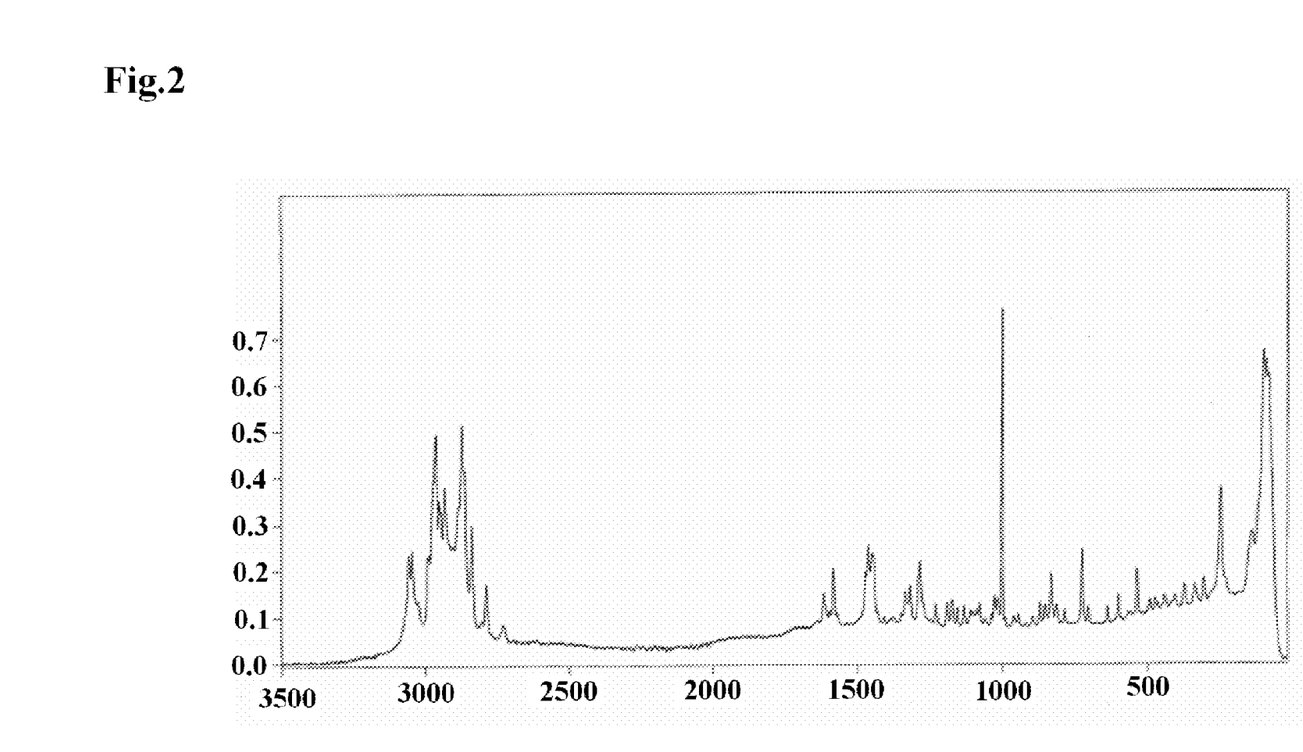
FIG. 2 shows a Raman spectrum of crystalline modification A.

FIG. 2 shows a Raman spectrum for modification A.

A further aspect of the invention relates to a method for the production of crystalline modification A, comprising the steps of:

(a) concentrating a solution of (1R,2R)-3-(3-dimethylamino-1-ethyl-2-methyl-propyl)-phenol and (b) storing the residue obtained in step (a) at a temperature of >5° C.

To produce crystalline modification A, a solution of (1R,2R)-3-(3-dimethylamino-1-ethyl-2-methyl-propyl)-phenol is initially preferably fully concentrated.

Conventional organic solvents known to persons skilled in the art may be used as solvents in a solution of this type, in particular alcohols such as methanol, ethanol, 1-propanol and 2-propanol, esters such as ethyl acetate, ketones such as acetone and ethylmethyl ketone, ethers such as diethyl ether, tert-butyl methyl ether, 1,4-dioxane and tetrahydrofuran, nitriles such as acetonitrile, chlorinated hydrocarbons such as dichloromethane, aromatic hydrocarbons such as toluene, and also dimethyl formamide and dimethyl sulfoxide. Saturated hydrocarbons, such as n-pentane, n-hexane and n-heptane, and water are less suitable, the compound (1R,2R)-3-(3-dimethylamino-1-ethyl-2-methyl-propyl)-phenol being only poorly soluble in these substances.

The solution may also be concentrated by conventional methods known to persons skilled in the art, for example on a rotary evaporator or in an inert gas flow, in particular in an argon flow or nitrogen flow.

Normally, a preferably oily residue remains after concentration and crystallizes out in the form of modification A after storage at a temperature of >5° C. In general, a storage time of 24 hours is sufficient.

Further treatment, where necessary, can also be carried out by conventional methods known to persons skilled in the art, for example by filtration, washing and/or drying.

A further aspect of the invention relates to a crystalline modification A of (1R,2R)-3-(3-dimethylamino-1-ethyl-2-methyl-propyl)-phenol which can be obtained by the method described above.

In another aspect, the invention relates to a crystalline modification B of (1R,2R)-3-(3-dimethylamino-1-ethyl-2-methyl-propyl)-phenol.

This crystalline modification B according to the invention of (1R,2R)-3-(3-dimethylamino-1-ethyl-2-methyl-propyl)-phenol has an X-ray diffraction peak at $29.06\pm0.20$ (2Θ).

Preferably, the crystalline modification B according to the invention may additionally have at least one X-ray diffraction peak selected from the group consisting of $19.50\pm0.20$ (2Θ), $35.49\pm0.20$ (2Θ) and $40.01\pm0.20$ (2Θ).

The crystalline modification B according to the invention may further be characterized in that as well as the X-ray diffraction peak at $29.06\pm0.20$ (2Θ) and optionally one or more X-ray diffraction peaks selected from the group consisting of $19.50\pm0.20$ (2Θ), $35.49\pm0.20$ (2Θ) and $40.01\pm0.20$ (2Θ), it additionally has at least one X-ray diffraction peak selected from the group consisting of $14.11\pm0.20$ (2Θ), $14.44\pm0.20$ (2Θ), $16.08\pm0.20$ (2Θ), $17.17\pm0.20$ (2Θ), $17.43\pm0.20$ (2Θ), $18.81\pm0.20$ (2Θ), $20.24\pm0.20$ (2Θ), $20.80\pm0.20$ (2Θ), $22.00\pm0.20$ (2Θ), $22.49\pm0.20$ (2Θ), $23.40\pm0.20$ (2Θ), $24.15\pm0.20$ (2Θ), $24.51\pm0.20$ (2Θ) and $29.89\pm0.20$ (2Θ).

Furthermore, the crystalline modification B according to the invention may be characterized in that as well as the X-ray diffraction peak at $29.06\pm0.20$ (2Θ) and optionally one or more X-ray diffraction peaks selected from the group consisting of $19.50\pm0.20$ (2Θ), $35.49\pm0.20$ (2Θ) and $40.01\pm0.20$ (2Θ) and optionally one or more X-ray diffraction peaks selected from the group consisting of $14.11\pm0.20$ (2Θ), $14.44\pm0.20$ (2Θ), $16.08\pm0.20$ (2Θ), $17.17\pm0.20$ (2Θ), $17.43\pm0.20$ (2Θ), $18.81\pm0.20$ (2Θ), $20.24\pm0.20$ (2Θ), $20.80\pm0.20$ (2Θ), $22.00\pm0.20$ (2Θ), $22.49\pm0.20$ (2Θ), $23.40\pm0.20$ (2Θ), $24.15\pm0.20$ (2Θ), $24.51\pm0.20$ (2Θ) and $29.89\pm0.20$ (2Θ), it additionally has at least one X-ray diffraction peak selected from the group consisting of $18.67\pm0.20$ (2Θ), $25.24\pm0.20$ (2Θ), $25.36\pm0.20$ (2Θ), $27.58\pm0.20$ (2Θ), $27.79\pm0.20$ (2Θ), $30.11\pm0.20$ (2Θ) and $31.00\pm0.20$ (2Θ).

The crystalline modification B according to the invention may also be characterized in that as well as the X-ray diffraction peak at $29.06\pm0.20$ (2Θ) and optionally one or more X-ray diffraction peaks selected from the group consisting of $19.50\pm0.20$ (2Θ), $35.49\pm0.20$ (2Θ) and $40.01\pm0.20$ (2Θ) and optionally one or more X-ray diffraction peaks selected from the group consisting of $14.11\pm0.20$ (2Θ), $14.44\pm0.20$ (2Θ), $16.08\pm0.20$ (2Θ), $17.17\pm0.20$ (2Θ), $17.43\pm0.20$ (2Θ), $18.81\pm0.20$ (2Θ), $20.24\pm0.20$ (2Θ), $20.80\pm0.20$ (2Θ), $22.00\pm0.20$ (2Θ), $22.49\pm0.20$ (2Θ), $23.40\pm0.20$ (2Θ), $24.15\pm0.20$ (2Θ), $24.51\pm0.20$ (2Θ) and $29.89\pm0.20$ (2Θ) and optionally one or more X-ray diffraction peaks selected from the group consisting of $18.67\pm0.20$ (2Θ), $25.24\pm0.20$ (2Θ), $25.36\pm0.20$ (2Θ), $27.58\pm0.20$ (2Θ), $27.79\pm0.20$ (2Θ), $30.11\pm0.20$ (2Θ) and $31.00\pm0.20$ (2Θ), it has at least one X-ray diffraction peak selected from the group consisting of $22.85\pm0.20$ (2Θ), $24.88\pm0.20$ (2Θ), $30.31\pm0.20$ (2Θ), $31.17\pm0.20$ (2Θ), $31.54\pm0.20$ (2Θ), $32.11\pm0.20$ (2Θ), $32.45\pm0.20$ (2Θ), $32.76\pm0.20$ (2Θ), $33.61\pm0.20$ (2Θ), $33.94\pm0.20$ (2Θ), $35.95\pm0.20$ (2Θ), $36.54\pm0.20$ (2Θ), $37.12\pm0.20$ (2Θ), $37.32\pm0.20$ (2Θ), $37.75\pm0.20$ (2Θ) $38.13\pm0.20$ (2Θ), $38.72\pm0.20$ (2Θ) and $39.63\pm0.20$ (2Θ).

Preferably, the crystalline modification B according to the invention is also characterized in that it does not have one or more of the following X-ray diffraction peaks selected from the group consisting of $10.93\pm0.20$ (2Θ), $12.41\pm0.20$ (2Θ), and $26.22\pm0.20$ (2Θ).

It is also preferable for the crystalline modification B according to the invention to also be characterized in that it does not have one or more of the following X-ray diffraction peaks selected from the group consisting of $8.10\pm0.20$ (2Θ), $10.93\pm0.20$ (2Θ), $11.83\pm0.20$ (2Θ), $12.41\pm0.20$ (2Θ), $26.22\pm0.20$ (2Θ), $26.54\pm0.20$ (2Θ) and $26.72\pm0.20$ (2Θ).

Figure 3:
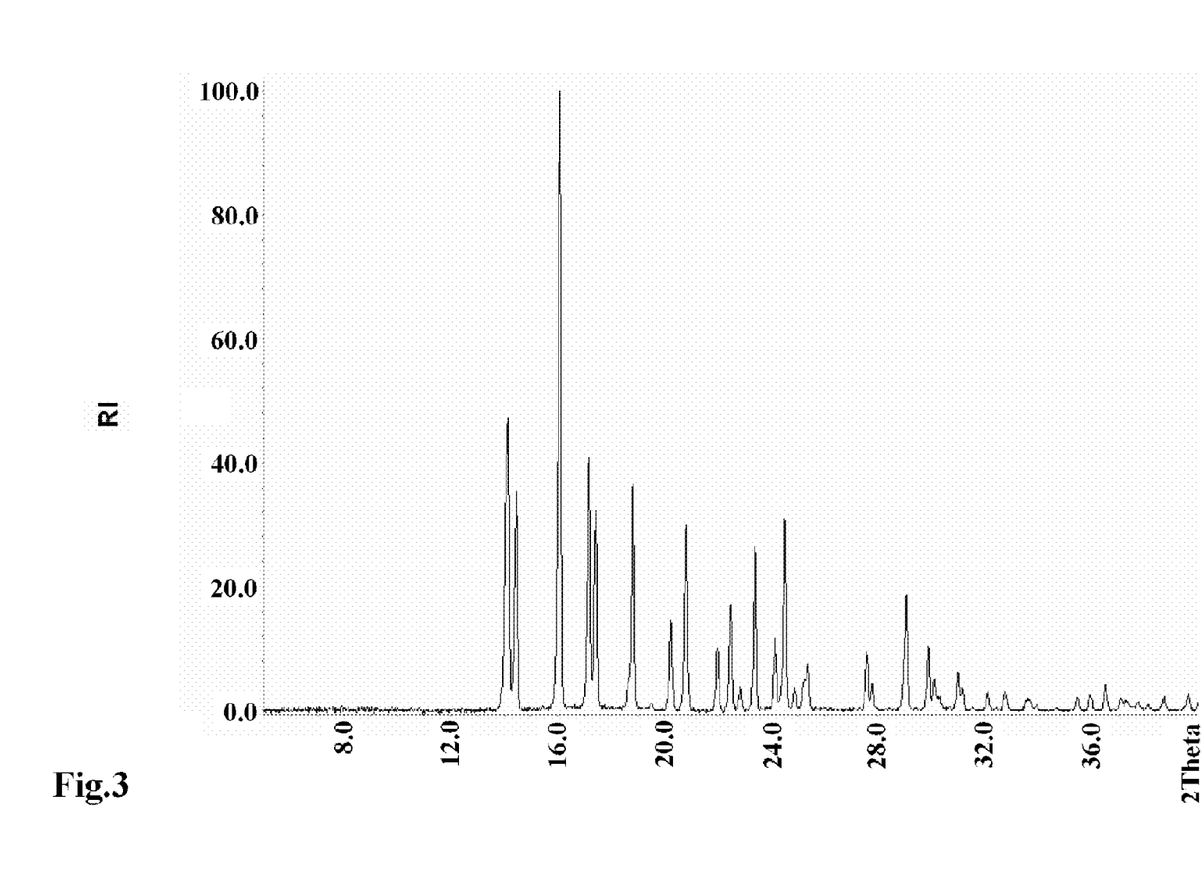
FIG. 3 shows an XRPD spectrum of crystalline modification B.

FIG. 3 shows an X-ray powder diffractogram of form B.

In DSC analyses, the crystalline modification B according to the invention preferably exhibits endothermy with a peak temperature at 87-93° C., more preferably at 88-92° C., even more preferably at 89-91° C.

Figure 4:
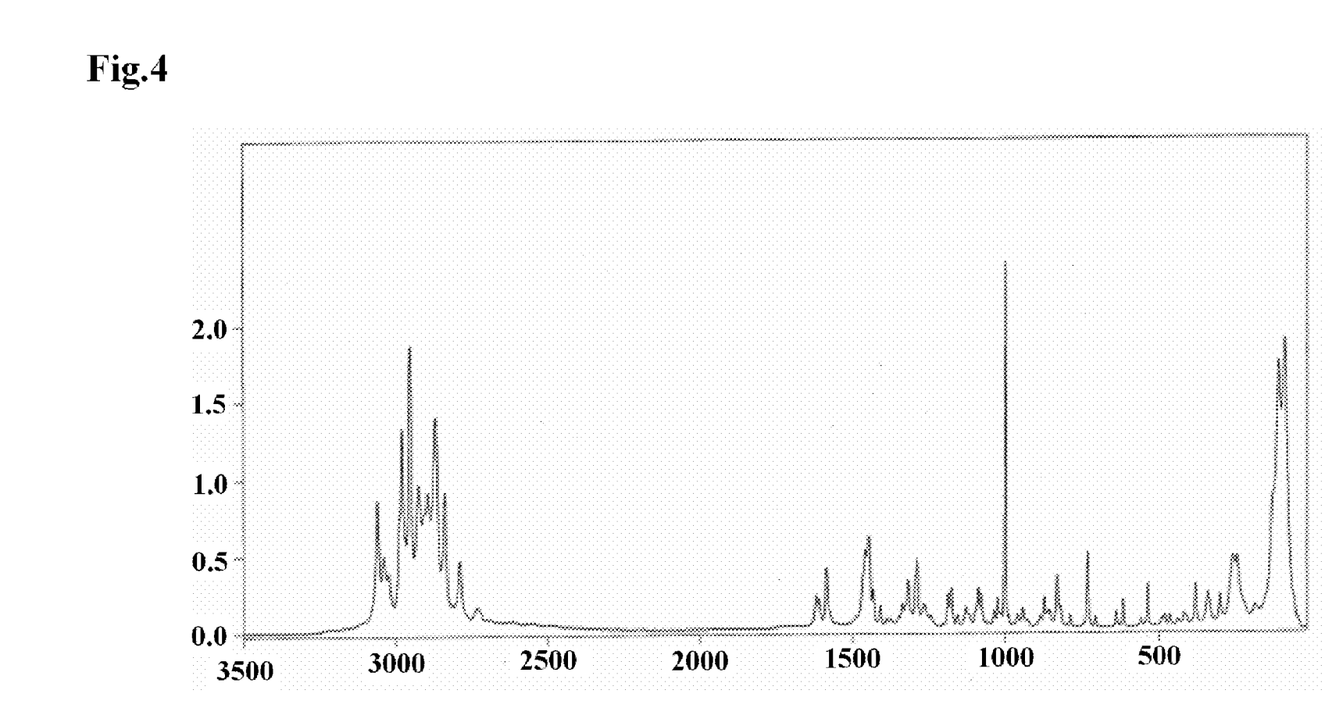
FIG. 4 shows a Raman spectrum of crystalline modification B.

The crystalline form B according to the invention is further characterized in that it has one or more Raman bands selected from the group consisting of $91\pm2$ cm$^{-1}$, $112\pm2$ cm$^{-1}$, $259\pm2$ cm$^{-1}$, $381\pm2$ cm$^{-1}$, $535\pm2$ cm$^{-1}$, $730\pm2$ cm$^{-1}$, $829\pm2$ cm$^{-1}$, $999\pm2$ cm$^{-1}$, $1088\pm2$ cm$^{-1}$, $1173\pm2$ cm$^{-1}$, $1288\pm2$ cm$^{-1}$, $1445\pm2$ cm$^{-1}$, $1585\pm2$ cm$^{-1}$, $2790\pm2$ cm$^{-1}$, $2838\pm2$ cm$^{-1}$, $2869\pm2$ cm$^{-1}$, $2925\pm2$ cm$^{-1}$, $2952\pm2$ cm$^{-1}$, $2980$ cm$^{-1}$ and $3059\pm2$ cm$^{-1}$. FIG. 4 shows a Raman spectrum for form B.

A further aspect of the invention relates to a method for the production of crystalline modification B, comprising the steps of:
(a) concentrating a solution of (1R,2R)-3-(3-dimethylamino-1-ethyl-2-methyl-propyl)-phenol and
(b1) storing the residue obtained in step (a) at a temperature of ≦5° C., or
(b2) suspending the residue obtained in step (a) and stirring this suspension.

To produce crystalline modification B, a solution of (1R,2R)-3-(3-dimethylamino-1-ethyl-2-methyl-propyl)-phenol is initially preferably fully concentrated.

Conventional organic solvents known to persons skilled in the art may be used as solvents in a solution of this type, in particular alcohols such as methanol, ethanol, 1-propanol and 2-propanol, esters such as ethyl acetate, ketones such as acetone and ethylmethyl ketone, ethers such as diethyl ether, tert-butyl methyl ether, 1,4-dioxane and tetrahydrofuran, nitriles such as acetonitrile, chlorinated hydrocarbons such as dichloromethane, aromatic hydrocarbons such as toluene, and also dimethyl formamide and dimethyl sulfoxide. Saturated hydrocarbons, such as n-pentane, n-hexane and n-heptane, and water are less suitable, the compound (1R,2R)-3-(3-dimethylamino-1-ethyl-2-methyl-propyl)-phenol being only poorly soluble in these substances.

The solution may also be concentrated by conventional methods known to persons skilled in the art, for example on a rotary evaporator or in an inert gas flow, in particular in an argon flow or nitrogen flow.

Normally, a preferably oily residue remains after concentration and crystallizes out in the form of modification B after storage at a temperature of ≦5° C. In general, a storage time of 24 hours is sufficient.

Alternatively, the preferably oily residue may also be received in a suitable suspension medium and stirred for some time. Mixtures of one of the aforementioned solvents with water or a saturated hydrocarbon, in particular n-pentane, n-hexane or n-heptane, are particularly suitable as suspension media, and the proportion of solvent is to be selected in such a way that the residue is not completely dissolved.

The temperature in step (b) may vary over a wide range, in particular in the range of 5-25° C., just like the stirring time, which may vary from a few minutes to a number of weeks, in particular up to one week.

A further aspect of the invention relates to a method for the production of crystalline modification B, comprising the step of:
(a) precipitating (1R,2R)-3-(3-dimethylamino-1-ethyl-2-methyl-propyl)-phenol from solution.

Conventional organic solvents known to persons skilled in the art may be used to produce the (1R,2R)-3-(3-dimethylamino-1-ethyl-2-methyl-propyl)-phenol solution, in particular alcohols such as methanol, ethanol, 1-propanol and 2-propanol, esters such as ethyl acetate, ketones such as acetone and ethylmethyl ketone, ethers such as diethyl ether, tert-butyl methyl ether, 1,4-dioxane and tetrahydrofuran, nitriles such as acetonitrile, chlorinated hydrocarbons such as dichloromethane, aromatic hydrocarbons such as toluene, and also dimethyl formamide and dimethyl sulfoxide.

The (1R,2R)-3-(3-dimethylamino-1-ethyl-2-methyl-propyl)-phenol is then precipitated from the solution using media in which this compound is only poorly soluble, such as saturated hydrocarbons, such as n-pentane, n-hexane and n-heptane, and water, for example.

Further treatment, where necessary, can also be carried out by conventional methods known to persons skilled in the art, for example by filtration, washing and/or drying.

Crystalline modification B may also be obtained by cooling a melt of crystalline modification A.

A further aspect of the invention relates to a crystalline modification B of (1R,2R)-3-(3-dimethylamino-1-ethyl-2-methyl-propyl)-phenol which can be obtained by the methods disclosed above.

Normally, modification A is obtained by faster crystallization and/or at higher temperatures (probably via the amorphous form as an intermediate stage). Modification B is normally obtained by slower crystallization and/or at lower temperatures (probably by direct crystallization). Modification B has the most thermodynamically stable form, in particular in the temperature range of 5-85° C., preferably 5-50° C.

The thermodynamic stability is important. By using the most stable modification in a medicament it may specifically be ensured that, during storage, no polymorphic conversion of the active ingredient in the pharmaceutical formulation takes place. This is advantageous because otherwise the properties of the medicament could change as a consequence of a conversion of a less stable modification into a more stable modification. In relation to the pharmacological properties of an administration form, this could lead for example to the solubility of the active ingredient changing, accompanied by a change in the release characteristics and thus also a change in the bioavailability. Lastly, this could result in inadequate storage stability of the administration form.

A further aspect of the invention relates to crystalline modification C of (1R,2R)-3-(3-dimethylamino-1-ethyl-2-methyl-propyl)-phenol.

This crystalline modification C according to the invention of (1R,2R)-3-(3-dimethylamino-1-ethyl-2-methyl-propyl)-phenol has at least one X-ray diffraction peak selected from the group consisting of 10.93±0.20 (2Θ), 12.41±0.20 (2Θ) and 26.22±0.20 (2Θ).

Preferably, the crystalline modification C according to the invention may additionally have at least one X-ray diffraction peak selected from the group consisting of 8.10±0.20 (2Θ), 11.83±0.20 (2Θ), 26.54±0.20 (2Θ) and 26.72±0.20 (2Θ).

The crystalline modification C according to the invention may further be characterized in that as well as at least one X-ray diffraction peak selected from the group consisting of 10.93±0.20 (2Θ), 12.41±0.20 (2Θ) and 26.22±0.20 (2Θ) and optionally one or more X-ray diffraction peaks selected from the group consisting of 8.10±0.20 (2Θ), 11.83±0.20 (2Θ), 26.54±0.20 (2Θ) and 26.72±0.20 (2Θ), it additionally has at least one X-ray diffraction peak selected from the group consisting of 13.71±0.20 (2Θ), 14.13±0.20 (2Θ), 14.82±0.20 (2Θ), 15.34±0.20 (2Θ), 15.59±0.20 (2Θ), 16.10±0.20 (2Θ) 16.43±0.20 (2Θ), 16.91±0.20 (2Θ), 17.32±0.20 (2Θ), 17.58±0.20 (2Θ), 17.82±0.20 (2Θ), 18.01±0.20 (2Θ), 18.46±0.20 (2Θ), 19.05±0.20 (2Θ), 20.23±0.20 (2Θ), 20.71±0.20 (2Θ), 20.94±0.20 (2Θ), 21.17±0.20 (2Θ), 21.90±0.20 (2Θ), 22.23±0.20 (2Θ), 22.52±0.20 (2Θ), 23.32±0.20 (2Θ), 24.12±0.20 (2Θ), 24.39±0.20 (2Θ), 24.92±0.20 (2Θ), 25.35±0.20 (2Θ), 27.33±0.20 (2Θ), 27.63±0.20 (2Θ), 27.84±0.20 (2Θ), 28.48±0.20 (2Θ), 29.64±0.20 (2Θ), 29.94±0.20 (2Θ), 30.54±0.20 (2Θ), 30.68±0.20 (2Θ), 31.03±0.20 (2Θ), 31.52±0.20 (2Θ), 32.29±0.20 (2Θ), 32.93±0.20 (2Θ), 33.66±0.20 (2Θ), 35.52±0.20 (2Θ), 36.05±0.20 (2Θ), 36.64±0.20 (2Θ), 37.54±0.20 (2Θ), 38.45±0.20 (2Θ), 39.15±0.20 (2Θ) and 40.05±0.20 (2Θ).

Figure 5:
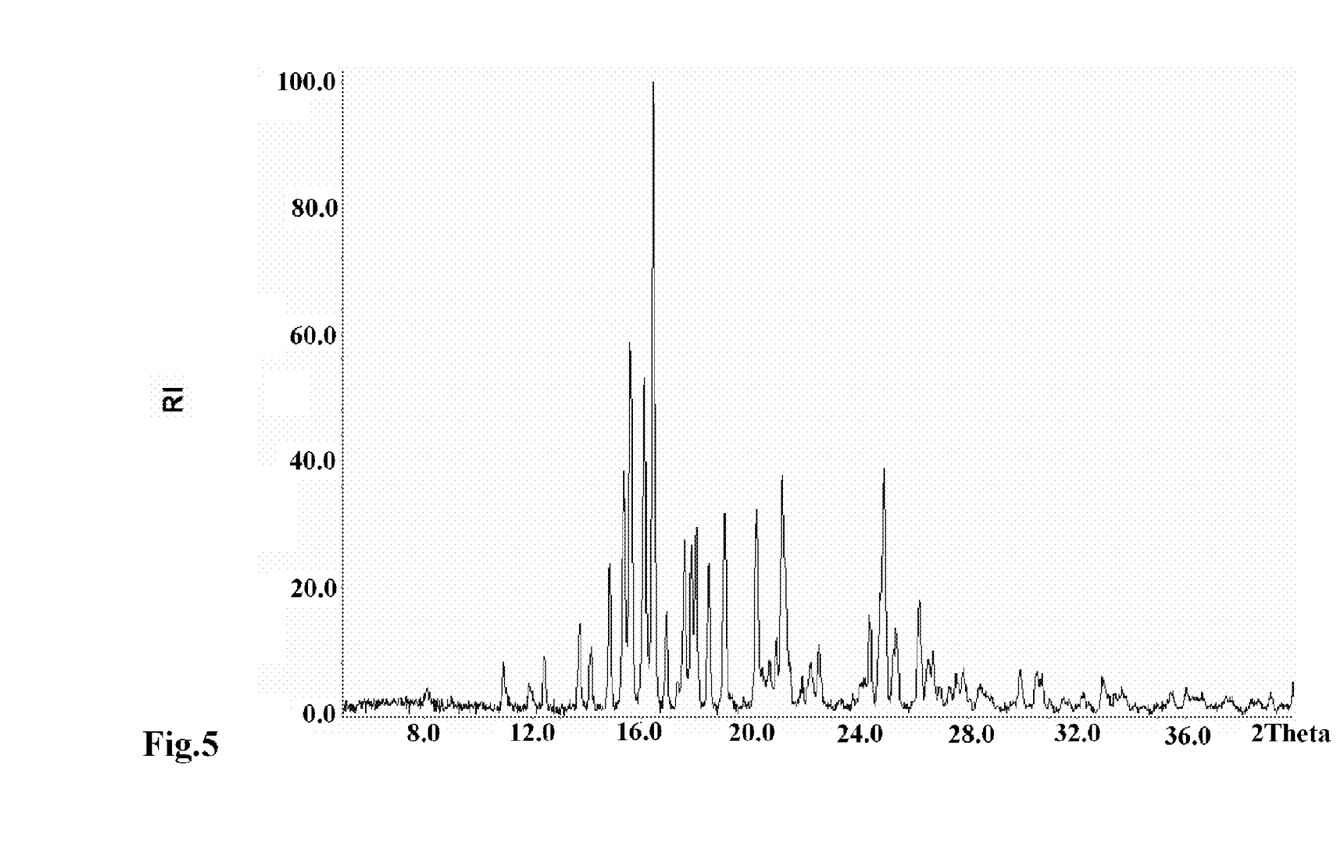
FIG. 5 shows an XRPD spectrum of crystalline modification C.

FIG. 5 shows an X-ray powder diffractogram of form C.

In DSC analyses, the crystalline modification C according to the invention preferably exhibits endothermy with a peak temperature at 75-84° C., more preferably at 76-83° C., even more preferably at 77-82° C., and in particular at 78-81° C. and/or endothermy with a peak temperature at 87-93° C., more preferably at 88-92° C., even more preferably at 89-91° C.

A further aspect of the invention relates to a method for the production of the aforementioned crystalline modification C, comprising the steps of:

(a) shaking a suspension containing crystalline modification A and/or crystalline modification B of (1R,2R)-3-(3-dimethylamino-1-ethyl-2-methyl-propyl)-phenol, and
(b) evaporating the suspension medium in an air flow.

Alcohols, in particular methanol, as well as aromatic hydrocarbons, in particular toluene, are particularly suitable suspension media.

In step a), the suspension is preferably shaken at a temperature which is above room temperature (20-25° C.), for example at a temperature in the range from >25 to 35° C., preferably 30±3° C., particularly preferably 30±2° C. and in particular 30±1° C. The shaking procedure preferably lasts for 1-6 hours, preferably 2-5 hours, even more preferably 3-4 hours.

Subsequently, the suspension medium is evaporated in an air flow, optionally after cooling the suspension to room temperature, and the resulting residue is optionally stored at room temperature.

Further treatment, where necessary, can also be carried out by conventional methods known to persons skilled in the art, for example by filtration, washing and/or drying.

A further aspect of the invention relates to a crystalline modification C of (1R,2R)-3-(3-dimethylamino-1-ethyl-2-methyl-propyl)-phenol which can be obtained by the method described above.

The modifications A, B and C according to the invention may optionally also form co-crystals and solvates. These are all included within the scope of the invention.

Another aspect of the invention is a pharmaceutical composition containing the active ingredient (1R,2R)-3-(3-dimethylamino-1-ethyl-2-methyl-propyl)-phenol in crystalline form and at least one pharmaceutically acceptable carrier.

Preferably, the pharmaceutical composition according to the invention may contain a polymorph selected from the group consisting of modification A, modification B and modification C.

It is also particularly preferable for the pharmaceutical composition according to the invention to contain modification A.

It is particularly preferable for the pharmaceutical composition according to the invention to contain modification B.

A further aspect of the present invention is a pharmaceutical administration form containing a pharmaceutical composition according to the invention as disclosed above.

Another aspect of the invention is a crystalline modification according to the invention of (1R,2R)-3-(3-dimethylamino-1-ethyl-2-methyl-propyl)-phenol, in particular a crystalline modification A, B or C according to the invention as disclosed above, as a drug.

A further aspect of the invention relates to the use of an effective pain alleviating amount of at least one crystalline modification according to the invention of (1R,2R)-3-(3-dimethylamino-1-ethyl-2-methyl-propyl)-phenol, in particular a crystalline modification A, B or C according to the invention in a medicament for the treatment of pain, in particular acute pain and chronic pain.

As well as at least one crystalline form A, form B or form C according to the invention or a mixture of at least two of these forms, the medicament according to the invention may, as is conventional, contain further pharmaceutically acceptable additives or excipients, such as substrates, fillers, solvents, thinning agents, colourings and/or binders.

The selection of the excipients and the amounts thereof to be used depend on whether the drug is to be applied orally, subcutaneously, parenterally, intravenously, intraperitoneally, intradermally, intramuscularly, intranasally or topically, for example to infections on the skin, mucous membranes and eyes. Preparations in the form of tablets, dragées, capsules, granules, drops, juices and syrups are particularly suitable for oral application, and solutions, suspensions, easily reconstitutable dry preparations and sprays for parenteral, topical and inhalative application. Crystalline forms according to the invention in a deposit in a dissolved form or in a plaster, optionally along with skin penetration enhancers, are suitable preparations for percutaneous application. Preparation forms which are to be applied orally or percutaneously may release the crystalline form according to the invention in a delayed manner.

The amount of active ingredient to be administered to patients can vary and is for example dependent on the weight of the patient, the type of application, the indication and the severity of the illness.

EXAMPLES

The invention will be illustrated in further detail with reference to examples which are merely illustrative and do not limit the scope of the invention.

The following abbreviations are used in the examples:

| | |
|---|---|
| RT | Room temperature, preferably 20-25° C. |
| TBME | tert-butyl methyl ether |
| EtOH | ethanol |
| MEK | 2-butanon |
| THF | tetrahydrofuran |
| 2PrOH | 2-propanol |
| EtOAc | ethyl acetate |
| MeCN | acetonitrile |
| DMSO | dimethyl sulfoxide |
| DMF | dimethyl formamide |
| IR | infra-red |
| min | minute |
| sec | second |

Unless otherwise specified, solvent mixtures are always volume/volume.

A) Synthesis of Modification A

A1)

16.689 g (1R,2R)-3-(3-dimethylamino-1-ethyl-2-methyl-propyl)-phenol, hydrochloride (which can be obtained in accordance with the provisions of EP A 0 693 475) were dissolved in 81 ml distilled water in a 250 ml three-necked flask and 32% by weight sodium hydroxide solution was added at room temperature until a pH value of 11 was reached (approx. 7 ml). Even after a few ml were added, a tough, white substance was precipitated and this was dissolved in approx. 16 ml ethyl acetate. After the addition was complete, a white suspension was achieved and was subsequently stirred for 1 hour. The pH value fell to 10 in the process and a further 0.5 ml sodium hydroxide solution was added. Subsequently, the precipitated base was extracted with a total of 288 ml ethyl acetate. The combined organic phases were then washed with approx. 32 ml water, dried over magnesium sulfate and concentrated in a vacuum on a rotary evaporator until dry.

A yellow oil remained in the flask and also did not crystallize at room temperature. Crystallization was then initiated by breaking the flask with a spatula and the oil crystallized within a few minutes in the form of a yellow residue. This residue was then crushed in a mortar and an off-white crystalline solid of modification A, characterized by $^1$H-NMR, DSC, TG-FTIR, XRPD, Raman and HPLC, was obtained.

Part of the resulting crystalline solid thus obtained was recrystallized as follows: 30 mg of modification A were weighed into a 20 ml vessel, 6 ml 2-propanol were added and shaken for 4 hours at 400 rpm at 30° C. Subsequently, the solvent was evaporated off in an air flow at 23° C. A white crystalline solid of form A was obtained.

A2)
200 mg of (1) according to B) were dissolved in 25 ml acetonitrile. Subsequently, the solvent was removed in a vacuum on a rotary evaporator. A colourless oil remained. Approx. 1 ml seed crystals of form A were added to this oil and the sample was stored at room temperature for 2 days. A crystalline solid of form A was obtained.

B) Synthesis of Modification B
B1)
3192 g of (2R,3R)-[3-(3-methoxy-phenyl)-2-methyl-pentyl]-dimethylamine were first obtained, in the form of the free base, from 3300 g (2R,3R)-[3-(3-methoxy-phenyl)-2-methyl-pentyl]-dimethylamine, hydrobromide (which can be obtained in accordance with the provisions of EP A 0 693 475) with 45% by weight sodium hydroxide solution (acid consumption=4.11 mol/kg).

18.9 kg of methanesulfonic acid and 2458 g D,L methionine were placed in methyl cyclohexane and then 3192 g (2R,3R)-[3-(3-methoxy-phenyl)-2-methyl-pentyl]-dimethylamine were added and the mixture was stirred at 82° C. for 18 hours. Subsequently, dilution was carried out with 10.3 l water at a maximum of 80° C. and 9 l methyl cyclohexane were added. At a maximum of 42° C., 17.3 l ammoniac were added until the pH was 8.8. A phase separation took place at 45° C. and 3.2 g (1R,2R)-3-(3-dimethylamino-1-ethyl-2-methyl-propyl)-phenol were added to the organic phase at 40° C. and stirred for 1 hour at 36° C. Subsequently, after cooling slowly to 5° C. and a further hour of stirring, the precipitate which formed was extracted by suction, washed with 12 l methyl cyclohexane and dried in a drying chamber. 2685 g (89.5%) (1R,2R)-3-(3-dimethylamino-1-ethyl-2-methyl-propyl)-phenol were obtained in modification B.

The compound of modification B thus obtained will be referred to in the following as (1).

C) Synthesis of Modification C
C1)
48.6 mg modification B were suspended in 10 ml methanol and shaken with a vortexer for 4 hours at 400 rpm at 30° C. After cooling to RT, the solvent was evaporated off at RT in an air flow.

After 24 hours, the residue was present as a mixture of oil and solid. After further storage (72 hours, sealed, room temperature), a white solid was obtained.

C2)
30.23 mg modification A were suspended in 6 ml toluene and shaken with a vortexer for 4 hours at 400 rpm at 30° C. After cooling to RT, the solvent was evaporated off at 23° C. in an air flow. A white solid was obtained.

The peak temperatures found in DSC analyses for the products obtained in accordance with C1) and C2) were in the range of 78-82° C. and 87-90° C. and thus in the range of the peak temperatures found for modifications A and B. The products could thus be a mixture of forms A and B. However, the powder diffractogram shows x-ray diffraction peaks which could not originate from a mixture of modifications A and B.

Crystallization Tests

Example 1

Amorphous (1R,2R)-3-(3-dimethylamino-1-ethyl-2-methyl-propyl)-phenol was obtained by rapid evaporation of a solution of the compound on a rotary evaporator. The oily residues were stored at RT or at 5° C. All the samples crystallized within 24 hours. Modification A or mixtures of modification A and modification B were obtained at RT. At lower temperatures (5° C.), modification B was obtained.

1.1) 109.1 mg (1) were dissolved in 2 ml TBME. The solvent was removed on a rotary evaporator. A colourless oil was obtained. The residue was stored overnight at RT. A mixture of modifications A and B was obtained.

1.2) 100 mg (1) were dissolved in 2 ml EtOH. The solvent was removed on a rotary evaporator. A colourless oil was obtained. The residue was stored overnight at RT. Modification A was obtained.

1.3) 105.6 mg (1) were dissolved in 2 ml EtOAc. The solvent was removed on a rotary evaporator. A colourless oil was obtained. The residue was stored overnight at RT. A mixture of modifications A and B was obtained.

1.4) 100.9 mg (1) were dissolved in 2 ml acetone. The solvent was removed on a rotary evaporator. A colourless oil was obtained. The residue was stored overnight at 5° C. Modification B was obtained.

1.5) 100.0 mg (1) were dissolved in 2 ml MEK. The solvent was removed on a rotary evaporator. A colourless oil was obtained. The residue was stored overnight at 5° C. Modification B was obtained.

1.6) 99.5 mg (1) were dissolved in 2 ml THF. The solvent was removed on a rotary evaporator. A colourless oil was obtained. The residue was stored overnight at 5° C. Modification B was obtained.

Example 2

Amorphous (1R,2R)-3-(3-dimethylamino-1-ethyl-2-methyl-propyl)-phenol was obtained by rapid evaporation of a solution of the compound on a rotary evaporator or in a nitrogen flow. The oily residues were suspended in various solvents and the mixtures thus obtained were stirred at RT or at 5° C. No formation of solvates was observed in the selected solvents.

2.1) 96.9 mg (1) were dissolved in 1 ml THF. The solution was filtered and subsequently the solvent was removed at RT under a strong nitrogen flow. 500 µl TBME were added to the residue thus obtained. The mixture was stirred at RT for a duration of 2 weeks. All solid components were dissolved.

2.2) 104.2 mg (1) were dissolved in 1 ml THF. The solution was filtered and subsequently the solvent was removed at RT under a strong nitrogen flow. 500 µl TBME were added to the residue thus obtained. The mixture was stirred at RT for a duration of 2 weeks. All solid components were dissolved.

2.3) 99.9 mg (1) were dissolved in 1 ml THF. The solution was filtered and subsequently the solvent was removed at RT under a strong nitrogen flow. 500 µl $H_2O$ were added to the residue thus obtained. The mixture was stirred at RT for a duration of 1 week. The resulting crystalline residue was filtered out. Modification B was obtained.

2.4) 95.3 mg (1) were dissolved in 1 ml THF. The solution was filtered and subsequently the solvent was removed at RT under a strong nitrogen flow. 500 µl IPE were added to the residue thus obtained. The mixture was stirred at RT for a duration of 2 weeks. All solid components were dissolved.

2.5) 101.7 mg (1) were dissolved in 1 ml THF. The solution was filtered and subsequently the solvent was removed at RT under a strong nitrogen flow. 500 µl $H_2O$/EtOH (1:1) were added to the residue thus obtained. The mixture was stirred at RT for a duration of 1 week. The resulting crystalline residue was filtered out. Modification B was obtained.

2.6) 101.0 mg (1) were dissolved in 1 ml THF. The solution was filtered and subsequently the solvent was removed at RT under a strong nitrogen flow. 500 µl acetone/EtOH (1:1) were added to the residue thus obtained. The mixture was stirred at RT for a duration of 2 weeks. Two liquid phases formed.

2.7) 96.9 mg (1) were dissolved in 1 ml THF. The solution was filtered and subsequently the solvent was removed at RT under a strong nitrogen flow. 500 µl TBME were added to the residue thus obtained. The mixture was stirred at 5° C. for a duration of 2 weeks. All solid components were dissolved.

2.8) 109.0 mg (1) were dissolved in 1 ml THF. The solution was filtered and subsequently the solvent was removed at RT under a strong nitrogen flow. 500 µl heptane/TBME (1:1) were added to the residue thus obtained. The mixture was stirred at a temperature of 5° C. for a duration of 1 week. The resulting crystalline residue was filtered out. Modification B was obtained.

2.9) 98.5 mg (1) were dissolved in 1 ml THF. The solution was filtered and subsequently the solvent was removed at RT under a strong nitrogen flow. 500 µl $H_2O$ were added to the residue thus obtained. The mixture was stirred at a temperature of 5° C. for a duration of 1 week. The resulting crystalline residue was filtered out. A mixture of modifications A and B was obtained.

2.10) 100.7 mg (1) were dissolved in 1 ml THF. The solution was filtered and subsequently the solvent was removed at RT under a strong nitrogen flow. 500 µl IPE were added to the residue thus obtained. The mixture was stirred at 5° C. for a duration of 2 weeks. All solid components were dissolved.

2.11) 96.7 mg (1) were dissolved in 1 ml THF. The solution was filtered and subsequently the solvent was removed at RT under a strong nitrogen flow. 500 µl EtOH/$H_2O$ (1:1) were added to the residue thus obtained. The mixture was stirred at a temperature of 5° C. for a duration of 1 week. The resulting crystalline residue was filtered out. Modification B was obtained.

2.12) 105.1 mg (1) were dissolved in 1 ml THF. The solution was filtered and subsequently the solvent was removed at RT under a strong nitrogen flow. 500 µl acetone/$H_2O$ (1:1) were added to the residue thus obtained. The mixture was stirred at a temperature of 5° C. for a duration of 1 week. The resulting crystalline residue was filtered out. Modification B was obtained.

Example 3

Crystallization tests were carried out by vapor diffusion, using saturated hydrocarbons and ethers as precipitants. Only in one case was a crystalline precipitate obtained, namely modification B.

3.1) 200 mg (1) were dissolved in 2 ml 2PrOH. The solution was stored at RT in a saturated n-hexane atmosphere for a duration of 8 weeks. No precipitate was obtained.

3.2) 200 mg (1) were dissolved in 2 ml EtOAc. The solution was stored at RT in a saturated n-hexane atmosphere for a duration of 8 weeks. No precipitate was obtained.

3.3) 200 mg (1) were dissolved in 2 ml toluene. The solution was stored at RT in a saturated n-hexane atmosphere for a duration of 8 weeks. No precipitate was obtained.

3.4) 200 mg (1) were dissolved in 2 ml THF. The solution was stored at RT in a saturated n-hexane atmosphere for a duration of 8 weeks. The crystal precipitate which formed was filtered off. Modification B was obtained.

3.5) 200 mg (1) were dissolved in 2 ml 2PrOH. The solution was stored at RT in a saturated IPE atmosphere for a duration of 8 weeks. No precipitate was obtained.

3.6) 200 mg (1) were dissolved in 2 ml EtOAc. The solution was stored at RT in a saturated IPE atmosphere for a duration of 8 weeks. No precipitate was obtained.

3.7) 200 mg (1) were dissolved in 2 ml toluene. The solution was stored at RT in a saturated IPE atmosphere for a duration of 8 weeks. No precipitate was obtained.

3.8) 200 mg (1) were dissolved in 2 ml THF. The solution was stored at RT in a saturated IPE atmosphere for a duration of 8 weeks. No precipitate was obtained.

3.9) 200 mg (1) were dissolved in 2 ml 2PrOH. The solution was stored at RT in a saturated TBME atmosphere for a duration of 8 weeks. No precipitate was obtained.

3.10) 200 mg (1) were dissolved in 2 ml EtOAc. The solution was stored at RT in a saturated TBME atmosphere for a duration of 8 weeks. No precipitate was obtained.

3.11) 200 mg (1) were dissolved in 2 ml toluene. The solution was stored at RT in a saturated TBME atmosphere for a duration of 8 weeks. No precipitate was obtained.

3.12) 200 mg (1) were dissolved in 2 ml THF. The solution was stored at RT in a saturated TBME atmosphere for a duration of 8 weeks. No precipitate was obtained.

3.13) 200 mg (1) were dissolved in 1 ml EtOAc. The solution was stored at RT in a saturated cyclohexane atmosphere for a duration of 1 week. No precipitate was obtained. The sample was stored at 5° C. for a duration of two weeks. No precipitate was obtained.

3.14) 200 mg (1) were dissolved in 3 ml MeCN. The solution was stored at RT in a saturated cyclohexane atmosphere for a duration of 1 week. No precipitate was obtained. The sample was stored at 5° C. for a duration of two weeks. No precipitate was obtained.

3.15) 200 mg (1) were dissolved in 1 ml DMSO. The solution was stored at RT in a saturated cyclohexane atmosphere for a duration of 3 weeks. No precipitate was obtained.

3.16) 200 mg (1) were dissolved in 1 ml EtOAc. The solution was stored at RT in a saturated pentane atmosphere for a duration of 1 week. No precipitate was obtained. The sample was stored at 5° C. for a duration of two weeks. No precipitate was obtained.

3.17) 200 mg (1) were dissolved in 3 ml MeCN. The solution was stored at RT in a saturated pentane atmosphere for a duration of 1 week. No precipitate was obtained. The sample was stored at 5° C. for a duration of two weeks. No precipitate was obtained.

3.18) 200 mg (1) were dissolved in 1 ml DMSO. The solution was stored at RT in a saturated pentane atmosphere for a duration of 3 weeks. No precipitate was obtained.

Example 4

4.1) 100 mg (1) were dissolved in 1 ml EtOAc. 2 ml acetone were added incrementally until the solution became cloudy. The sample was stored at 5° C. for a duration of 10 days. No change was observed.

4.2) 100 mg (1) were dissolved in 0.5 ml 1,4-dioxane. 2 ml $H_2O$ were added incrementally until the solution became cloudy and an adhesive resin was precipitated. The sample was stored at 5° C. overnight. After scratching with a spatula, the resin crystallized out and the crystalline solid was filtered out. Modification B was obtained.

4.3) 100 mg (1) were dissolved in 0.5 ml EtOAc. 6 ml heptane were added incrementally until the solution became cloudy and a colourless solid was precipitated. The sample was stored at 5° C. for a duration of 6 days and the obtained solid was filtered out. A crystalline powder was obtained.

4.4) 100 mg (1) were dissolved in 1 ml dioxane. 3 ml heptane were added incrementally until the solution became cloudy. The sample was stored at 5° C. for a duration of 1 week. No change was observed.

4.5) 100 mg (1) were dissolved in 1 ml dioxane. 11 ml iBuOAc were added incrementally. No precipitate was obtained. The sample was stored at 5° C. for a duration of 1 week. No change was observed.

4.6) 100 mg (1) were dissolved in 1 ml EtOAc. 1 ml pentane was added incrementally until the solution became cloudy. The sample was stored at 5° C. for a duration of 1 week. No change was observed.

4.7) 100 mg (1) were dissolved in 2.5 ml MeOH. 3 ml $H_2O$ were added incrementally until the solution became cloudy and a colourless solid was precipitated. The sample was stored at RT for a duration of 1 week and the obtained solid was filtered out. A crystalline powder of modification A was obtained.

4.8) 100 mg (1) were dissolved in 500 µl 2PrOH. 3 ml $H_2O$ were added incrementally and the mixture was stirred at RT for a duration of 5 days. The obtained solid was filtered out. A crystalline powder of modification B was obtained.

4.9) 100 mg (1) were dissolved in 500 µl EtOH. 3 ml $H_2O$ were added incrementally and the mixture was stirred at RT for a duration of 5 days. The obtained solid was filtered out. A crystalline powder of modification B was obtained.

4.10) 100 mg (1) were dissolved in 1 ml DMF. 2 ml $H_2O$ were added incrementally and the mixture was stirred at RT for a duration of 5 days. The obtained solid was filtered out. A crystalline powder of modification B was obtained.

4.11) 100 mg (1) were dissolved in 1 ml DMSO. 1 ml $H_2O$ was added incrementally and the mixture was stirred at RT for a duration of 5 days. The obtained solid was filtered out. A crystalline powder of modification B was obtained.

4.12) 100 mg (1) were dissolved in 500 µl EtOAc. 2 ml pentane were added incrementally and the mixture was stirred at RT for a duration of a few hours. An adhesive solid formed. The sample was stored at 5° C. for a duration of 3 weeks and the obtained solid was filtered out.

4.13) 100 mg (1) were dissolved in 500 µl EtOAc. 2 ml n-hexane were added incrementally and the mixture was stirred at RT for a duration of a few hours. An adhesive solid formed. The sample was stored at 5° C. for a duration of 2 weeks and the obtained solid was filtered out. A crystalline powder of modification B was obtained.

4.14) 100 mg (1) were dissolved in 500 µl EtOAc. 2 ml n-heptane were added incrementally and the mixture was stirred at RT for a duration of a few hours. An adhesive solid formed. The sample was stored at 5° C. for a duration of 2 weeks and the obtained solid was filtered out. A crystalline powder of modification B was obtained.

4.15) 100 mg (1) were dissolved in 500 µl EtOAc. 2 ml n-cyclohexane were added incrementally and the mixture was stirred at RT for a duration of a few hours. An adhesive solid formed. The sample was stored at 5° C. for a duration of 2 weeks and the obtained solid was filtered out. A crystalline powder was obtained.

Example 5

5.1) The solution obtained in accordance with example 2.1) was stored at RT in an open vessel in order to evaporate off the solvent. After 1 week, a crystalline solid of modification A was obtained.

5.2) The solution obtained in accordance with example 2.2) was stored at RT in an open vessel in order to evaporate off the solvent. After 1 week, a crystalline solid of modification A was obtained.

5.3) The solution obtained in accordance with example 2.4) was stored at RT in an open vessel in order to evaporate off the solvent. After 1 week, a crystalline solid of modification A was obtained.

5.4) The solution obtained in accordance with example 2.6) was stored at RT in an open vessel in order to evaporate off the solvent. After 1 week, a crystalline solid of modification A was obtained.

5.5) The solution obtained in accordance with example 2.7) was stored at RT in an open vessel in order to evaporate off the solvent. After 2 days, a crystalline solid of modification B was obtained.

5.6) The solution obtained in accordance with example 2.10) was stored at RT in an open vessel in order to evaporate off the solvent. After 2 days, a crystalline solid of modification B was obtained.

5.7) The solution obtained in accordance with example 4.1) was stored at RT in an open vessel in order to evaporate off the solvent. After 2 days, a crystalline solid of modification A was obtained.

5.8) The solution obtained in accordance with example 4.4) was stored at RT in an open vessel in order to evaporate off the solvent. After 6 days, a crystalline solid of modification A was obtained.

5.9) The solution obtained in accordance with example 4.5) was stored at RT in an open vessel in order to evaporate off the solvent. After 6 days, a crystalline solid of modification B was obtained.

5.10) The solution obtained in accordance with example 4.6) was stored at RT in an open vessel in order to evaporate off the solvent. After 6 days, a crystalline solid of modification B was obtained.

Example 6

The crystalline modification B of (1R,2R)-3-(3-dimethylamino-1-ethyl-2-methyl-propyl)-phenol exhibited no change upon suspension in various solvents. It was possible to exclude the formation of solvates with the selected solvents.

6.1) 200 mg (1) were suspended in 500 µl TBME. The mixture was stirred at RT for a duration of 2 days and the resulting solid was filtered out. A crystalline powder of modification B was obtained.

6.2) 100 mg (1) were suspended in 500 µl heptane/TBME (1:1). The mixture was stirred at RT for a duration of 2 days and the resulting solid was filtered out. A crystalline powder of modification B was obtained.

6.3) 100 mg (1) were suspended in 500 µl $H_2O$. The mixture was stirred at RT for a duration of 2 days and the resulting solid was filtered out. A crystalline powder of modification B was obtained.

6.4) 100 mg (1) were suspended in 500 μl IPE. The mixture was stirred at RT for a duration of 2 days and the resulting solid was filtered out. A crystalline powder of modification B was obtained.

6.5) 100 mg (1) were suspended in 500 μl H₂O/EtOH. The mixture was stirred at RT for a duration of 2 days and the resulting solid was filtered out. A crystalline powder of modification B was obtained.

Example 7

Attempts were made to produce the amorphous modification of (1R,2R)-3-(3-dimethylamino-1-ethyl-2-methyl-propyl)-phenol by evaporation, lyophilization or melting. All obtained samples of the amorphous modification crystallized within hours.

7.1) 150 mg (1) were dissolved in 3 ml MeOH. The solvent was removed on a rotary evaporator. A colourless oil remained. The residue was dried in a vacuum. Modification A was obtained.

7.2) 150 mg (1) were dissolved in 2 ml 1,4-dioxane. The solvent was removed by freeze-drier. Modification A was obtained.

7.3) 150 mg (1) were dissolved in 2 ml 1,4-dioxane. The solvent was removed by freeze-drier (−85° C., 0.5 mbar). A colourless residue remained and crystallized spontaneously before it was possible to perform a PXRD analysis. Modification B was obtained with traces of modification A.

7.4) 150 mg (1) were melted at 88-91° C. The melt was frozen with dry ice. An amorphous film was obtained which crystallized within 1 hour.

Example 8

The effect of mechanical stress from grinding with a ball mill (model Retsch MM200, agate vessel and agate ball with 5 mm diameter) and from pressure during the production of a tablet was analysed. Although the pressure during compaction had no effect on the samples, modification A was converted into modification B when ground.

8.1) A tablet was produced with 100 mg (1) on an IR tablet press (pressure 10 t, 30 min). Modification B was obtained.

8.2) A tablet was produced with 100 mg of the product of modification A according to example 5.8 on an IR tablet press (pressure 10 t, 30 min). Modification A was obtained.

8.3) 16 mg of the crystalline modification B were ground in a ball mill (shaking frequency: 30 sec⁻¹, RT) as follows: 2×90 min, 1×60 min, 2×30 min discontinuation. Modification B was obtained.

8.4) 15 mg of the crystalline form A were ground in a ball mill (shaking frequency: 30 sec$^{-1}$, RT) as follows: 2×90 min, 1×60 min, 2×30 min discontinuation. Modification B was obtained.

Example 9

9.1) 20.5 mg modification A and 20.9 mg modification B were suspended in 200 μl IPE. The suspension was shaken overnight in an Eppendorf Thermomixer at RT. The obtained solid was filtered out and characterized by FT Raman spectral analysis. Modification B was obtained.

9.2) 19.8 mg modification A and 20.5 mg modification B were suspended in 300 μl acetone/H₂O (8:2). The suspension was shaken overnight in an Eppendorf Thermomixer at RT. The resulting solid was filtered out and characterized by FT Raman spectral analysis. Modification B was obtained.

9.3) 15 mg modification A and 20.5 mg modification B were suspended in 1 ml acetone/H₂O (8:2). The suspension was stirred for three days at 5° C. The obtained solid was filtered out and characterized by FT Raman spectral analysis. Modification B was obtained.

9.4) 20.5 mg modification A and 20.9 mg modification B were suspended in 200 μl IPE. The suspension was stirred overnight at 50° C. The obtained solid was filtered out and characterized by FT Raman spectral analysis. Modification B was obtained.

9.5) 15 mg modification A and 15 mg modification B were suspended in 1 ml acetone/H₂O (8:2). The suspension was stirred overnight at 50° C. The obtained solid was filtered out and characterized by FT Raman spectral analysis. Modification B was obtained.

9.6) 20.5 mg modification A and 20.9 mg modification B were suspended in 200 μl IPE. The suspension was stirred overnight at 50° C. All solid components were dissolved. After cooling to RT, small amounts of a colourless solid were precipitated. The solvent was removed in a nitrogen flow. Modification B was obtained.

Analysis—XRPD (X-Ray Powder Diffraction=XRPD):

XRPD analyses were carried out in transmission geometry with a STOE Stadi P X-ray powder diffractometer, monochromatised CuKα$_1$ radiation being used by means of a germanium monocrystal. d-distances were calculated from the 2Θ values, establishing the wavelength of 1.54060 Å. In general, the 2Θ values have an error rate of ±0.2° in 2Θ. The experimental error in the d-distance values is therefore dependent on the location of the peak.

Modification A

Table 1 shows the peak list for modification A. The uncertainty in the 2Θ values is ±0.2° in 2Θ; rel. I (or RI) is the relative intensity of the respective peaks. Maximum intensity is 100.

TABLE 1

| 2Θ | rel. I |
| --- | --- |
| 13.71 | 30 |
| 14.11 | 9 |
| 14.80 | 45 |
| 15.58 | 100 |
| 16.31 | 3 |
| 16.89 | 18 |
| 17.79 | 37 |
| 18.45 | 34 |
| 19.07 | 8 |
| 20.20 | 15 |
| 20.92 | 12 |
| 21.12 | 5 |
| 21.90 | 7 |
| 22.21 | 6 |
| 22.50 | 18 |
| 23.30 | 3 |
| 24.04 | 2 |
| 24.37 | 17 |
| 24.75 | 9 |
| 25.33 | 18 |
| 27.32 | 5 |
| 27.55 | 6 |
| 28.05 | 2 |
| 28.37 | 3 |
| 29.62 | 1 |
| 29.90 | 5 |
| 30.28 | 1 |
| 30.68 | 5 |
| 31.43 | 3 |
| 32.21 | 4 |
| 32.98 | 3 |
| 33.41 | 2 |
| 33.76 | 1 |
| 34.17 | 1 |
| 34.45 | 1 |

TABLE 1-continued

| 2Θ | rel. I |
| --- | --- |
| 35.98 | 2 |
| 36.24 | 2 |
| 36.54 | 1 |
| 36.87 | 1 |
| 37.06 | 2 |
| 37.48 | 2 |
| 37.87 | 1 |
| 38.64 | 3 |
| 39.48 | 2 |

Indexing the diffractogram for form A with the program WinXPow Index (Version 2.03) from STOE & Cie GmbH gave the following lattice constants, which correspond well with those which were established in a monocrystal structure determination: orthorhombic, a=12.92 Å, b=11.98 Å, c=8.98 Å, cell volume 1391 Å$^3$ Modification B Table 2 shows the peak list for modification B. The uncertainty in the 2Θ values is ±0.2° in 2Θ; rel. I is the relative intensity of the respective peaks. Maximum intensity is 100.

TABLE 2

| 2Θ | rel. I |
| --- | --- |
| 14.11 | 47 |
| 14.44 | 35 |
| 16.08 | 100 |
| 17.17 | 42 |
| 17.43 | 33 |
| 18.67 | 5 |
| 18.81 | 37 |
| 19.50 | 1 |
| 20.24 | 15 |
| 20.80 | 30 |
| 22.00 | 10 |
| 22.49 | 17 |
| 22.85 | 4 |
| 23.40 | 26 |
| 24.15 | 12 |
| 24.51 | 31 |
| 24.88 | 4 |
| 25.24 | 5 |
| 25.36 | 8 |
| 27.58 | 9 |
| 27.79 | 5 |
| 29.06 | 19 |
| 29.89 | 10 |
| 30.11 | 5 |
| 30.31 | 2 |
| 31.00 | 6 |
| 31.17 | 4 |
| 31.54 | 1 |
| 32.11 | 3 |
| 32.45 | 1 |
| 32.76 | 3 |
| 33.61 | 2 |
| 33.94 | 1 |
| 35.49 | 2 |
| 35.95 | 3 |
| 36.54 | 4 |
| 37.12 | 2 |
| 37.32 | 2 |
| 37.75 | 1 |
| 38.13 | 1 |
| 38.72 | 2 |
| 39.63 | 3 |
| 40.01 | 1 |

Indexing the diffractogram for form B with the program WinXPow Index (Version 2.03) from STOE & Cie GmbH gave the following lattice constants, which correspond well with those which were established in a monocrystal structure determination: orthorhombic, a=12.54 Å, b=12.27 Å, c=9.10 Å, cell volume 1400 Å$^3$ Modification C Table 3 shows the peak list for modification C. The uncertainty in the 2Θ values is ±0.2° in 2Θ; rel. I is the relative intensity of the respective peaks. Maximum intensity is 100.

TABLE 3

| 2Θ | Rel. I |
| --- | --- |
| 8.10 | 4 |
| 10.93 | 8 |
| 11.83 | 4 |
| 12.41 | 9 |
| 13.71 | 14 |
| 14.13 | 11 |
| 14.82 | 24 |
| 15.34 | 38 |
| 15.59 | 58 |
| 16.10 | 53 |
| 16.43 | 100 |
| 16.91 | 16 |
| 17.32 | 5 |
| 17.58 | 27 |
| 17.82 | 27 |
| 18.01 | 30 |
| 18.46 | 25 |
| 19.05 | 33 |
| 20.23 | 32 |
| 20.71 | 9 |
| 20.94 | 12 |
| 21.17 | 39 |
| 21.90 | 6 |
| 22.23 | 8 |
| 22.52 | 11 |
| 23.32 | 2 |
| 24.12 | 4 |
| 24.39 | 15 |
| 24.92 | 39 |
| 25.35 | 14 |
| 26.22 | 17 |
| 26.54 | 9 |
| 26.72 | 10 |
| 27.33 | 4 |
| 27.63 | 5 |
| 27.84 | 7 |
| 28.48 | 4 |
| 29.64 | 1 |
| 29.94 | 7 |
| 30.54 | 7 |
| 30.68 | 5 |
| 31.03 | 2 |
| 31.52 | 3 |
| 32.29 | 3 |
| 32.93 | 5 |
| 33.66 | 4 |
| 35.52 | 3 |
| 36.05 | 4 |
| 36.64 | 3 |
| 37.54 | 3 |
| 38.45 | 2 |
| 39.15 | 3 |
| 40.05 | 6 |

Analysis—DSC

Differential Scanning Calorimetry (DSC): device reference Perkin Elmer DSC 7 or Perkin Elmer Pyris 1. Unless otherwise specified, the samples were weighed in a sealed gold crucible. The measurement took place in a nitrogen flow in a temperature range from −50° C. to 250° C. with a heating rate of 10° C./min. The temperatures specified in relation to DSC analyses are, unless otherwise specified, the temperatures of the peak maxima (peak temperature $T_P$). Onset temperatures of peaks are indicated by $T_O$.

|  | DSC |
| --- | --- |
| Modification A | $T_O$ 77.83° C.; $T_P$ 79.46° C.; J/g 107.03 |
| Modification B | $T_O$ 88.60° C.; $T_P$ 89.76° C.; J/g 114.67 |
| Modification C | $T_O$ 78.72° C.; $T_P$ 81.00° C.; J/g 110.74 |
|  | $T_O$ 88.36° C.; $T_P$ 89.17° C.; J/g 0.57 |

Analysis—FT Raman Spectroscopy

Crystalline modifications A and B of (1R,2R)-3-(3-dimethylamino-1-ethyl-2-methyl-propyl)-phenol were each characterized by Fourier transform (FT) Raman spectrometry. For this purpose, the FT Raman spectra were recorded on a Bruker RFS100 Raman spectrometer (Nd-YAG 100 mW laser, excitation 1064 nm, Ge detector, 64 scans, 25-3500 cm$^{-1}$, resolution 2 cm$^{-1}$).

Analysis—TG-FTIR

Crystalline modifications A and B of (1R,2R)-3-(3-dimethylamino-1-ethyl-2-methyl-propyl)-phenol were each characterized by thermogravimetric Fourier transform infrared spectroscopy (TG-FTIR). For this purpose, the appropriate spectra were recorded with a Netzsch Thermo-Microwaage TG 209 and a Bruker FT-IR spectrometer Vector 22 (aluminium crucible (open or with micro-aperture), nitrogen atmosphere, heating rate 10° C./min, 25-250° C.). The TG-FTIR analyses showed that both modifications decompose above 160° C.

Analysis—DVS

Crystalline modifications A and B of (1R,2R)-3-(3-dimethylamino-1-ethyl-2-methyl-propyl)-phenol were each characterized by dynamic vapor sorption (DVS). The analyses were recorded in dynamic mode (5% relative air humidity/hour).

The DVS cycles are reversible. At a temperature of 25° C., changes in mass of 0.8% for modification A and 0.3% for modification B were found. Both modifications are not or at most slightly hygroscopic.

Analysis—Rate of Dissolution

To analyse the rate of dissolution of modifications A and B in water, two different determinations were carried out.

In the first determination, a suspension of modification A or B was in each case stirred in water, without taking into account the particle size distribution. Under these conditions, the particle size affects the result. Although form B is the more stable form at RT, it dissolves more rapidly.

In the second determination, a fresh sample of modification A was produced and tablets were produced for both modifications, A and B. Neither form was influenced by the compaction, but nevertheless, both samples exhibited a rate of dissolution of 0.003 mg/min cm$^2$. Analysis of the samples with FT Raman showed that form A had been converted into form B during the determination.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A crystalline modification of (1R,2R)-3-(3-dimethylamino-1-ethyl-2-methyl-propyl)-phenol selected from the group consisting of:
    crystalline modification A having X-ray diffraction peaks at 14.80±0.20 (2Θ), 15.58±0.20 (2Θ), 17.79±0.20 (2Θ) and 25.33±0.20 (2Θ);
    crystalline modification B having X-ray diffraction peaks at 14.11±0.20 (2Θ), 16.08±0.20 (2Θ), 17.17±0.20 (2Θ) and 29.06±0.20 (2Θ); and
    crystalline modification C having X-ray diffraction peaks at 10.93±0.20 (2Θ), 16.43±0.20 (2Θ), 21.17±0.20 (2Θ) and 24.92±0.20 (2Θ).

2. Crystalline modification A of (1R,2R)-3-(3-dimethylamino-1-ethyl-2-methyl-propyl)-phenol according to claim 1, having X-ray diffraction peaks at 14.80±0.20 (2Θ), 15.58±0.20 (2Θ), 17.79±0.20 (2Θ) and 25.33±0.20 (2Θ).

3. Crystalline modification A according to claim 2, further having at least one X-ray diffraction peak selected from the group consisting of 28.37±0.20 (2Θ) and 34.45±0.20 (2Θ).

4. Crystalline modification A according to either claim 2, further having at least one X-ray diffraction peak selected from the group consisting of 13.71±0.20 (2Θ), 16.89±0.20 (2Θ), 18.45±0.20 (2Θ), 20.20±0.20 (2Θ), 20.92±0.20 (2Θ), 22.50±0.20 (2Θ) and 24.37±0.20 (2Θ).

5. Crystalline modification A according to claim 2, further having at least one X-ray diffraction peak selected from the group consisting of 14.11±0.20 (2Θ), 19.07±0.20 (2Θ), 21.12±0.20 (2Θ), 21.90±0.20 (2Θ), 22.21±0.20 (2Θ), 24.75±0.20 (2Θ), 27.32±0.20 (2Θ), 27.55±0.20 (2Θ), 29.90±0.20 (2Θ) and 30.68±0.20 (2Θ).

6. Crystalline modification A according to claim 2, characterized by the absence of at least one X-ray diffraction peak selected from the group consisting of 8.10±0.20 (2Θ), 10.93±0.20 (2Θ), 11.83±0.20 (2Θ), 12.41±0.20 (2Θ), and 26.22±0.20 (2Θ), 26.54±0.20 (2Θ) and 26.72±0.20 (2Θ).

7. Crystalline modification A according to claim 2, which exhibits endothermy in the range of 75 to 84° C. in differential scanning calorimetry analysis.

8. A method for producing crystalline modification A according to claim 2, comprising:
    (a) concentrating a solution of (1R,2R)-3-(3-dimethylamino-1-ethyl-2-methyl-propyl)-phenol to obtain a residue, and
    (b) storing the residue from (a) at a temperature of >5° C.

9. Crystalline modification A of (1R,2R)-3-(3-dimethylamino-1-ethyl-2-methyl-propyl)-phenol obtained by the method of claim 8.

10. Crystalline modification B of (1R,2R)-3-(3-dimethylamino-1-ethyl-2-methyl-propyl)-phenol according to claim 1, having X-ray diffraction peaks at 14.11±0.20 (2Θ), 16.08±0.20 (2Θ), 17.17±0.20 (2Θ) and 29.06±0.20 (2Θ).

11. Crystalline modification B according to claim 10, further having at least one X-ray diffraction peak selected from the group consisting of 19.50±0.20 (2Θ), 35.49±0.20 (2Θ) and 40.01±0.20 (2Θ).

12. Crystalline modification B according to claim 10, further having at least one X-ray diffraction peak selected from the group consisting of 14.44±0.20 (2Θ), 17.43±0.20 (2Θ), 18.81±0.20 (2Θ), 20.24±0.20 (2Θ), 20.80±0.20 (2Θ), 22.00±0.20 (2Θ), 22.49±0.20 (2Θ), 23.40±0.20 (2Θ), 24.15±0.20 (2Θ), 24.51±0.20 (2Θ) and 29.89±0.20 (2Θ).

13. Crystalline modification B according to claim 10, further having at least one X-ray diffraction peak selected from the group consisting of 18.67±0.20 (2Θ), 25.24±0.20 (2Θ), 25.36±0.20 (2Θ), 27.58±0.20 (2Θ), 27.79±0.20 (2Θ), 30.11±0.20 (2Θ) and 31.00±0.20 (2Θ).

14. Crystalline modification B according to claim 10, characterized by the absence of at least one X-ray diffraction peak selected from the group consisting of 8.10±0.20 (2Θ), 10.93±0.20 (2Θ), 11.83±0.20 (2Θ), 12.41±0.20 (2Θ), 26.22±0.20 (2Θ), 26.54±0.20 (2Θ) and 26.72±0.20 (2Θ).

15. Crystalline modification B according to claim 10, which exhibits endothermy in the range of 87-93° C. in differential scanning calorimetry analysis.

16. A method for producing crystalline modification B according to claim 10, comprising:
(a) concentrating a solution of (1R,2R)-3-(3-dimethylamino-1-ethyl-2-methyl-propyl)-phenol to obtain a residue, and
(b1) storing the residue from (a) at a temperature of ≦5° C., or
(b2) suspending the residue from (a) in a liquid medium, and stirring the resulting suspension.

17. Crystalline modification B of (1R,2R)-3-(3-dimethylamino-1-ethyl-2-methyl-propyl)-phenol obtained by the method of claim 16.

18. A method for producing crystalline modification B according to claim 10, comprising precipitating (1R,2R)-3-(3-dimethylamino-1-ethyl-2-methyl-propyl)-phenol from solution.

19. Crystalline modification B of (1R,2R)-3-(3-dimethylamino-1-ethyl-2-methyl-propyl)-phenol obtained by the method of claim 18.

20. Crystalline modification C of (1R,2R)-3-(3-dimethylamino-1-ethyl-2-methyl-propyl)-phenol according to claim 1, having X-ray diffraction peaks at 10.93±0.20 (2Θ), 16.43±0.20 (2Θ), 21.17±0.20 (2Θ) and 24.92±0.20 (2Θ).

21. Crystalline modification C according to claim 20, further having at least one X-ray diffraction peak selected from the group consisting of 8.10±0.20 (2Θ), 11.83±0.20 (2Θ), 26.54±0.20 (2Θ) and 26.72±0.20 (2Θ).

22. Crystalline modification C according to claim 21, further having at least one X-ray diffraction peak selected from the group consisting of 13.71±0.20 (2Θ), 14.13±0.20 (2Θ), 14.82±0.20 (2Θ), 15.34±0.20 (2Θ), 15.59±0.20 (2Θ), 16.10±0.20 (2Θ), 16.91±0.20 (2Θ), 17.32±0.20 (2Θ), 17.58±0.20 (2Θ), 17.82±0.20 (2Θ), 18.01±0.20 (2Θ), 18.46±0.20 (2Θ), 19.05±0.20 (2Θ), 20.23±0.20 (2Θ), 20.71±0.20 (2Θ), 20.94±0.20 (2Θ), 21.90±0.20 (2Θ), 22.23±0.20 (2Θ), 22.52±0.20 (2Θ), 23.32±0.20 (2Θ), 24.12±0.20 (2Θ), 24.39±0.20 (2Θ), 25.35±0.20 (2Θ), 27.33±0.20 (2Θ), 27.63±0.20 (2Θ), 27.84±0.20 (2Θ), 28.48±0.20 (2Θ), 29.64±0.20 (2Θ), 29.94±0.20 (2Θ), 30.54±0.20 (2Θ), 30.68±0.20 (2Θ), 31.03±0.20 (2Θ), 31.52±0.20 (2Θ), 32.29±0.20 (2Θ), 32.93±0.20 (2Θ), 33.66±0.20 (2Θ), 35.52±0.20 (2Θ), 36.05±0.20 (2Θ), 36.64±0.20 (2Θ), 37.54±0.20 (2Θ), 38.45±0.20 (2Θ), 39.15±0.20 (2Θ) and 40.05±0.20 (2Θ).

23. Crystalline modification C according to claim 20, which exhibits endothermy with a peak temperature at 75-84° C., or endothermy with a peak temperature at 87-93° C., or both, in differential scanning calorimetry analysis.

24. A method for producing crystalline modification C according to claim 20, comprising:
(a) shaking a suspension containing at least one crystalline modification of (1R,2R)-3-(3-dimethylamino-1-ethyl-2-methyl-propyl)-phenol selected from the group consisting of crystalline modification A and crystalline modification B suspended in a suspension medium, and
(b) evaporating the suspension medium in an air flow.

25. Crystalline modification C of (1R,2R)-3-(3-dimethylamino-1-ethyl-2-methyl-propyl)-phenol obtained by the method of claim 24.

26. A pharmaceutical composition comprising at least one crystalline modification of (1R,2R)-3-(3-dimethylamino-1-ethyl-2-methyl-propyl)-phenol according to claim 1 selected from the group consisting of crystalline modification A, crystalline modification B and crystalline modification C and a pharmaceutically acceptable carrier.

27. A method of combating pain in a subject, said method comprising administering to said subject an effective pain alleviating amount of a crystalline modification of (1R,2R)-3-(3-dimethylamino-1-ethyl-2-methyl-propyl)-phenol according to claim 1 selected from the group consisting of crystalline modification A, crystalline modification B and crystalline modification C.

\* \* \* \* \*